(12) United States Patent
Amat Girbau et al.

(10) Patent No.: US 9,119,653 B2
(45) Date of Patent: Sep. 1, 2015

(54) ROBOTIC SYSTEM FOR LAPAROSCOPIC SURGERY

(75) Inventors: Josep Amat Girbau, Barcelona (ES); Alicia Casals Gelpi, Barcelona (ES); Manel Frigola Bourlon, Barcelona (ES)

(73) Assignee: UNIVERSITAT POLITECNICA DE CATALUNYA, Barcelona (ES)

( * ) Notice: Subject to any disclaimer, the term of this patent is extended or adjusted under 35 U.S.C. 154(b) by 763 days.

(21) Appl. No.: 13/321,802

(22) PCT Filed: May 20, 2010

(86) PCT No.: PCT/ES2010/000224
§ 371 (c)(1),
(2), (4) Date: Jan. 13, 2012

(87) PCT Pub. No.: WO2010/133733
PCT Pub. Date: Nov. 25, 2010

(65) Prior Publication Data
US 2012/0136372 A1   May 31, 2012

(30) Foreign Application Priority Data

May 22, 2009   (ES) .................................. 200901313

(51) Int. Cl.
*A61B 19/00* (2006.01)
(52) U.S. Cl.
CPC ..... *A61B 19/2203* (2013.01); *A61B 2019/2223* (2013.01)
(58) Field of Classification Search
CPC .... A61B 19/20; A61B 19/22; A61B 19/2203; A61B 19/26; A61B 17/00
USPC .................. 606/1, 10–16, 130; 600/101–108, 600/129–131; 901/1, 15–18, 27, 28, 30; 414/1–8, 744.1–744.7; 700/245
See application file for complete search history.

(56) References Cited

U.S. PATENT DOCUMENTS

| 4,068,156 A | 1/1978 | Johnson et al. |
| 4,859,139 A | 8/1989 | Torii |

(Continued)

FOREIGN PATENT DOCUMENTS

| CN | 1969772 A | 5/2007 |
| CN | 101160104 A | 4/2008 |

(Continued)

OTHER PUBLICATIONS

International Preliminary Report on Patentability and Written Opinion of the International Searching Authority—Translation—dated Nov. 22, 2011, for International Application No. PCT/ES2010/000224 (10 pages); the International Bureau (IB) of WIPO, Geneva Switzerland.

(Continued)

*Primary Examiner* — Ahmed Farah
(74) *Attorney, Agent, or Firm* — Peter B. Scull; Hamilton, DeSanctis & Cha LLP

(57) ABSTRACT

It comprises a supporting structure in which at least one arm is slidably attached. Each arm comprises first and second members hinged to each other. The first member is rotatably hinged to the supporting structure and it can be rotated about a longitudinal axis and the second member may receive a joint having at least two degrees of freedom for attaching a tool. The longitudinal axis of the first member is substantially perpendicular to an axis joining the first member and the second member to each other. A simplified architecture is obtained allowing for accurate and efficient spatial movement of the tool holding arm.

6 Claims, 3 Drawing Sheets

(56) References Cited

U.S. PATENT DOCUMENTS

| | | | |
|---|---|---|---|
| 4,921,393 | A | 5/1990 | Andeen |
| 5,762,458 | A | 6/1998 | Wang |
| 5,811,951 | A | 9/1998 | Young |
| 6,120,433 | A | 9/2000 | Mizuno et al. |
| 6,246,200 | B1 * | 6/2001 | Blumenkranz et al. .. 318/568.11 |
| 6,436,107 | B1 * | 8/2002 | Wang et al. .................. 606/139 |
| 7,155,316 | B2 | 12/2006 | Sutherland |
| 2003/0208186 | A1 | 11/2003 | Moreyra |
| 2004/0111183 | A1 | 6/2004 | Sutherland |
| 2009/0192521 | A1 | 7/2009 | Braun |

FOREIGN PATENT DOCUMENTS

| | | |
|---|---|---|
| ES | 2248066 T3 | 3/2006 |
| ES | 2264158 T3 | 12/2006 |
| JP | H07136173 A | 5/1995 |
| WO | 2006091494 A1 | 8/2006 |
| WO | 2007088206 A2 | 8/2007 |
| WO | WO2007088206 A2 | 9/2007 |
| WO | 2010050771 A2 | 5/2010 |

OTHER PUBLICATIONS

Translation of State Intellectual Property Office of the People's Republic of China, application No. 201080027584.1, applicant Universitat Politecnica De Catalunya, Notification of the First Office Action dated Sep. 30, 2013.

State Intellectual Property Office of the People's Republic of China, application No. 201080027584.1, applicant Universitat Politecnica De Catalunya, Notification of the First Office Action dated Sep. 30, 2013.

Translation of Notice of Reasons for Rejection issued by Japanese Patent Office, application No. 2012511310, dated issued Jan. 28, 2014.

Notice of Reasons for Rejection issued by Japanese Patent Office, application No. 2012511310, dated issued Jan. 28, 2014.

Faraz, et al., A Robotic Case Study: Optimal Design for Laparoscopic Positioning Stands, 1997 IEEE International Conference on Robotics and Automation, Apr. 20-25, 1997, pp. 1553-1560, vol. 2, IEEE, Piscataway, N.J., USA.

* cited by examiner

ROBOTIC SYSTEM FOR LAPAROSCOPIC SURGERY

TECHNICAL FIELD

A robotic system for holding and handling a surgical tool or instrument for surgery, particularly for minimally invasive laparoscopic surgery is herein disclosed. The present robotic system comprises a supporting structure to which one or more arms that can be remotely operated from a tele-operation station are slidably attached.

Each of said arms attached to the supporting structure is configured as an articulated assembly comprising two elements. Both elements are hinged to each other and, in turn, the first member can be rotated relative to the supporting structure.

BACKGROUND ART

The present robotic system finds general application in the field of robotic surgery and particularly in the field of minimally invasive surgery. In minimally invasive surgery smaller incisions are made as compared to those in conventional surgery that require a very precise operation of the surgical tool. Through these incisions surgical operations are carried out, including introducing of vision cameras (laparoscopy) for obtaining images of internal organs and transmitting them to a television monitor through which the surgeon can be guided to perform such surgical procedures.

These surgical procedures through robotic surgery are performed remotely by using tele-operation stations connected to a robotic system via dedicated communication lines.

Robotic systems include architectures designed to behave like a human arm, allowing a robot arm to be arranged in different positions. These architectures are formed by one or several arms mounted on a supporting structure and formed by hinged members so they can be moved properly in the space to operate a tool, terminal organ or end effector, such as a gripper or other device to perform surgical operations. Movement is driven by commands that are remotely received through the tele-operation station.

Each of said arms is an articulated structure comprising several members hinged to each other and rotatably mounted to the supporting structure. One example of robot arm architecture with articulated members is the robot known as Scara, with freedom of movement in the X and Y axes, although they are limited in their movements in the vertical axis Z, where simple and short-distance procedures are usually performed.

The limitations of these architectures are typically overcome through an intensive use of complex electronics and mechanisms in order to provide a robotic system suitable for minimally invasive surgery. This involves an undesirably costly robotic system due to complexity as a whole.

Document US2003208186 describes a robotic mechanism with three degrees of freedom comprising a supporting structure to which an arm is slidably attached vertically. The arm comprises a first member and a second member hinged to each other. The first member is in turn hinged to the supporting structure and by means of it a tool can be positioned. However, such architecture has the disadvantage that it does not allow the tool to be properly positioned in order to insert it by a surgical instrument (trocar).

Document U.S. Pat. No. 5,762,458 refers to a system for performing minimally invasive cardiac surgery procedures. This system comprises articulated arms adapted to handle a tool in space. Said arms have several degrees of freedom and, in one embodiment, they are provided with three motor driven joints (that can be driven in displacement and rotation), two passive joints and one motor driven joint that can be rotated for driving a tool placed at the arm end. This robotic system has the disadvantage that it does not allow for a fully effective positioning of the tool through the incision in the patient.

SUMMARY

A robotic system for laparoscopic surgery, particularly but not exclusively, for minimally invasive surgery is disclosed. The present robotic system has a substantially simpler construction than robotic systems used for the same purpose so far. In addition to the structural simplicity of the robotic system provided herein, the present robotic system for laparoscopic surgery has a particular architecture capable of properly positioning a tool, terminal organ or end effector, such as a gripper or device to perform surgical operations, with high mobility for being properly introduced through an incision in the patient.

The present robotic system for minimally invasive laparoscopic surgery comprises a supporting structure comprising a vertical column around which longitudinal axis arms can be rotated. The column may be mounted on a stationary platform that is preferably provided with wheels for ease of movement if necessary. One or more robotic arms are slidably attached vertically to the column. In the event that more than one robotic arm is provided on the supporting structure, said arms are attached such that they can be slidably displaced vertically in order to adjust their height from the ground and therefore allowing a surgical tool to be effectively positioned in a proper position.

Each of the arms of the robotic system comprises a first member and a second member. Both the first and second members are hinged to each other through a shaft or joint. On the other hand, the first member of the arm is rotatably mounted on the supporting structure and, in turn, said first member is adapted to be rotated about its longitudinal axis. Particularly, the first member of the arm is rotatably mounted on an extension integral with the supporting structure.

The second member of the robotic arm is adapted to receive a joint with at least two passive degrees of freedom at one end thereof for attaching a surgical tool or instrument. In the event that more than one robotic arm is provided, the arms can be rotated independently of each other around the longitudinal axis of the supporting structure. This architecture provides a significantly simplified assembly.

In some embodiments said joint having at least two degrees of freedom for attaching a tool may have three degrees of freedom, such as a gimbal-type joint. One-axis stability (usually in the axis of the tool or instrument direction) and spatial movement suitable for operations of the tool through the incision in the patient by introducing two passive degrees of freedom in the system are thus achieved.

Thus, the assembly is provided with a total of five degrees of freedom (four plus the supporting structure vertical displacement for positioning and manoeuvrability of the tool) so the tool can be always positioned in the direction defined by the penetration site into the cavity made in the patient (for example, the abdominal cavity) through the trocar.

In one embodiment, the longitudinal axis of the first member of the robotic arm can be at least substantially perpendicular to the joint axis of the first member and the second member.

The second member of the arm may comprise two rods arranged substantially parallel to each other and separated by a distance suitable for providing therein and hinged thereto one end of the first member of the arm. This allows collision free rotation of the first and the second members of the robotic arm.

Other objects, advantages and features of the present robotic system for minimally invasive laparoscopic surgery will be apparent from the description of a preferred embodiment. This description is given by way of non-limitative example and it is illustrated in the accompanying drawings.

DESCRIPTION OF ONE PREFERRED EMBODIMENT

Figure 1:
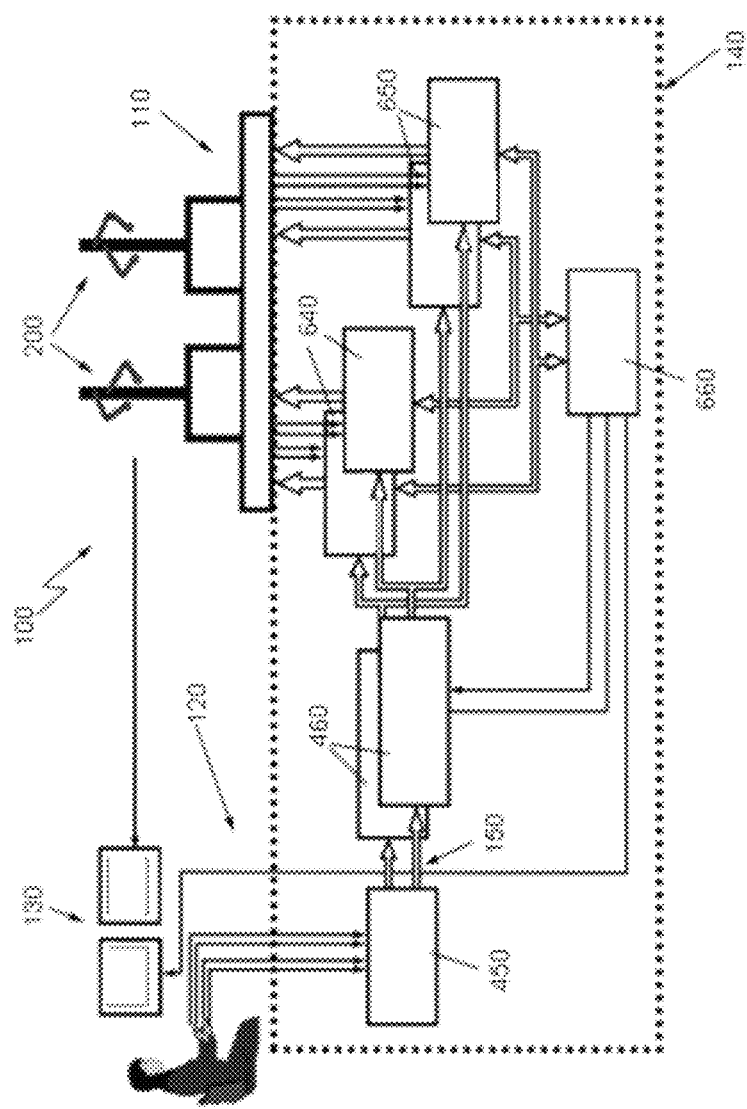
FIG. 1 is a diagram of a tele-operation system fitted with the present robotic system.

A tele-operation system 100 for performing minimally invasive laparoscopic surgery is shown in the figures. The tele-operation system 100 comprises a workstation 110 having two robotic systems 200 according to one embodiment and a tele-operation station 120 for operation and control of the robotic system 200. The tele-operation station 120 includes a three-dimensional control system 130 for displaying the workplace scene with a desired magnification factor (zoom) and a perspective that can be controlled through the movements of one of the available arms.

The operator's control commands can be converted by the tele-operation station 120 into the operation of the robotic system 200 enhancing the manual operator's capabilities and operations can be controlled for more reliability. This allows the articulated robotic arms 210, 220 of the robotic system 200 to be gesturally operated and controlled through the movements of the operator's arms. The movements that the operator is capable to perform with his/her two hands can be applied to any of the arms 210, 220, at will, with the help of auxiliary actuating pedals (not shown). The robotic arms 210, 220 of the robotic system 200 (shown in FIG. 3) can be electrically actuated for locating and positioning each of the tools, terminal organs or end effectors 900 (such as grippers or surgical devices suitable for performing operations).

The link between tele-operation station 120 and the robotic system 200 is performed through a control unit 140. The control unit 140 is configured by a computer network that allow for real time control of the path of the robotic arms 210, 220 and positioning of surgical tools 900 controlled by the arms 210, 220, so that they all times conform with the movements of the operator's commands. The control unit 140 also performs movement coordination in order to avoid collisions between the arms 210, 220, and monitoring and correcting of the paths thereof according to operator's predefined criteria. The control unit 140 allows the operation with floating reference axes, which are reset in position and orientation at the operator's will in order to facilitate operation of the task in the vertical field position, although the operation is performed within the abdominal capacity of the patient 600 in other positions. It also allows the scale factor to be changed in order to adjust centimeter movements in the actuation station into millimeter movements as necessary. Such unit 140 further allows restraints on the workload of each of the arms 210, 220 to be defined in order to increase safety of patient 600. Through the unit 140 it is also possible to display the usable working space of the arms 210, 220 in order to facilitate initial proper positioning thereof over the operating table 700 and over the patient 600.

The signal 150 received from the tele-operation station 120 through magnetic position sensors 450 provides information 460 about the paths of the tools 900. Other position detection means, such as potentiometric or inertial sensors are also possible. This allows operator's movement capability to be facilitated as well as the mechanical constraints of most common 6D actuators to be avoided. A control 640 of the robotic system 200 and a control 650 of the tools 900 as well as a control 660 to avoid collisions are thus made possible.

Figure 3:
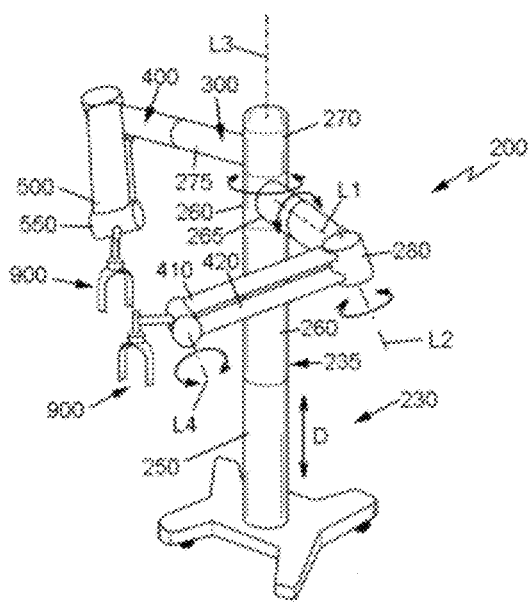
FIG. 3 is a perspective view of one embodiment of the present robotic system.

The workstation 110 comprises one or more robotic system 200 according to one embodiment. FIG. 3 shows one of said robotic systems 200 in detail. As it can be seen, each robotic system 200 comprises two arms 210, 220 mounted on a common supporting structure 230. Each arm 210, 220 has a load capacity such that forces up to 2.5 Kg can be applied and it is adapted to operate alongside the operating table 700, on either side thereof, or simultaneously using both of them, one on each side of the operating table 700. The arms 210, 220 of the robotic system 200 can be moved in space to cover an appropriate minimum working volume. The working volume is defined by a set of points where the tool 900 of each arm 210, 220 can be positioned, and corresponds to the volume enclosed by the surfaces determined by the points accessed by the tool 900 with its structure fully extended and fully retracted. In the structure of the embodiment, the minimum working volume corresponds to a hemisphere of radius 50 cm arranged centred on the same fixed centre but adjustable in height, and with accuracies of better than 1 mm.

Figure 2:
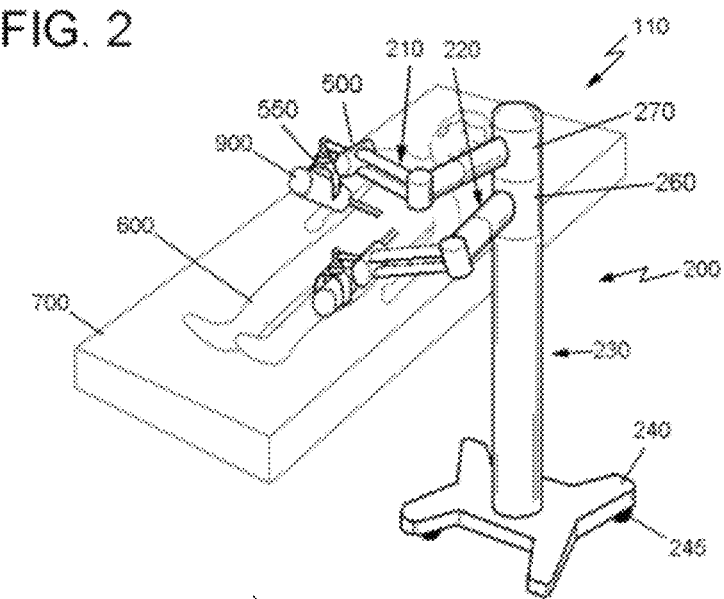
FIG. 2 is a perspective view of one embodiment of the present robotic system comprising a two-arm structure.

In the embodiment shown in FIGS. 2 and 3, the supporting structure 230 comprises a vertical column 235 fixed on a platform 240 having lockable wheels 245 for ease of movement. The platform 240 comprises a lower section 250 and two upper sections 260, 270, rotatably mounted to each other and to the lower section 250. The lower portion 250 of the supporting structure 230 is secured to the platform 240 for holding the robotic system 200 during operation. The upper sections 260, 270 of column 235 are mounted so that they can slide vertically according to the vertical direction indicated at D, that is, substantially perpendicular to the platform 240 of the supporting structure 230. The vertical linear displacement D of the upper sections 260, 270 allows the height of the robotic arms 210, 220 to the ground to be adjusted independently and thus the proper positioning of the tool 900.

For simplicity in the description the structure of one of the arms 210 of the robotic system 200 will be described below, although it will be understood that each of said arms 210, 220 has the same or a technically equivalent configuration.

The robotic arm 210 of the system described according to one embodiment comprises two members 300, 400 hinged to each other.

The first member 300 is an elongated body that is mounted on the supporting structure 230 so that it can be rotated about a longitudinal axis L1 of the first member 300. More specifically, this first member 300 is rotatably mounted on an extension 265 integral with the upper section 260 (the other robot arm 220 is rotatably mounted on the extension 275 corresponding to the upper section 270). The first member 300 can be thus rotated relative to the extension 265 of the upper section 260 of the robotic arm 210 around the longitudinal axis L1 and both arms 210, 220 can be rotated independently around the longitudinal axis L3 of the supporting structure 230, that is, the column 235.

The second member 400 of the robotic arm 210 is hinged to the first member 300 of the robotic arm 210 via a joint 280 so that they can be rotated about an axis L2, as it can be seen in FIG. 3. The longitudinal axis L1 of the first member 300 is substantially perpendicular to the axis L2 of the joint 280 of the first member 300 and the second member 400.

As it can be seen, the second articulated member 400 is formed with two rods 410, 420, which in the embodiment of the figures has an elliptical cross section. It will be understood, however, that the two rods 410, 420 may have other different geometries. The two rods 410, 420 are arranged parallel to each other spaced at a given distance in order to allow the second member 400 to be joined to one end of the first member 300 while preventing both members 300, 400, of the arm 210 from colliding with each other when rotating around axis L2 of the joint 280 arranged on a common end of both rods 410, 420 of the arm 210.

The opposite end 500 of both rods 410, 420 of the arm 210 is adapted for attaching of a surgical tool or instrument 900 through a pivot axis L4. The pivot axis L4 avoids collisions between the tool 900 and the rods 410, 420 of the second member 400 of the arm 210, 220. A mechanical joint 550 is provided at end 500 which allows the positioning of the tool 900 within the working space to be controlled in an appropriate manner for the operations through the incision in the patient 600. This mechanical joint 550 is a joint having two or more degrees of freedom adapted for attaching of the surgical tool or instrument 900. In the embodiment of the figures, the mechanical joint 550 is a joint having three degree of freedom, such as a gimbal-type joint. This allows two additional passive degrees of freedom to be introduced as well as one-axis stability (usually the positioning axis of tool 900) to be provided. The tool 900 can be therefore positioned always in a direction defined by the penetration site 950 into the cavity performed in the patient 600 (e.g. abdominal cavity), as shown in FIG. 4.

A manual adjustment fastening member for the trocars may be provided. This fastening member comprises a suspension member that may be manually attached to the supporting structure 230. At one end thereof two elements secured to this suspension member are supported through two manually lockable ball joints that allow the respective trocars to be fastened through a gimbal-type joint for reducing efforts performed with the surgical instrument or tool 900 on the patient's abdomen 600.

Figure 4:
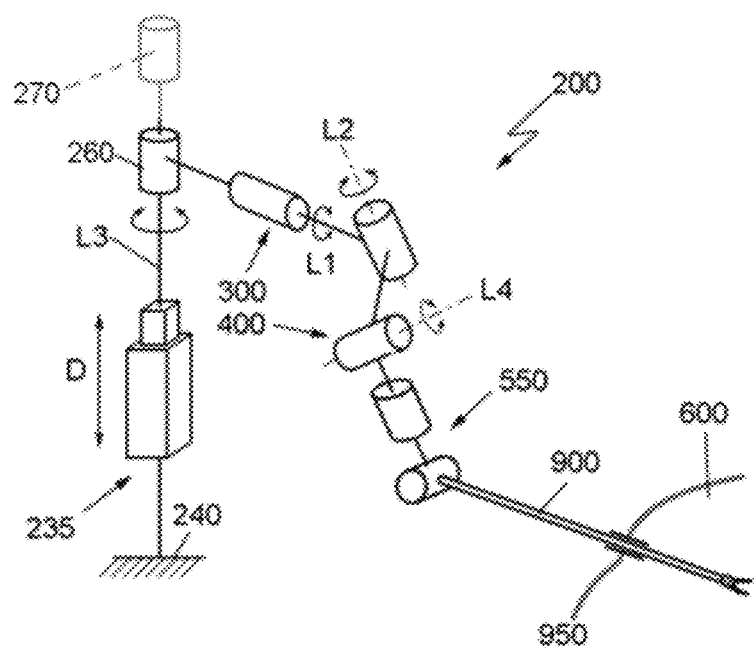
FIG. 4 is a diagrammatic view of the kinematic chain of the robotic system where the degrees of freedom are shown.

FIG. 4 schematically shows the kinematic chain of the mechanical structure of one embodiment of the present robotic system 200. As shown, each arm 210, 220 of the system 200 is an open kinematic chain of the D-G-G-G-G+ gimbal type with five degrees of freedom allowing for relative movement of the different elements 235, 300, 400, 900 between each two consecutive links of the structure.

Apart from the prismatic joint (vertical translational movement D), the four joints according to axes L1, L2, L3 and L4 are motor driven with the displacement D being shared by the two arms 210, 220.

Although embodiments of the present robotic system have been described in the specification and illustrated in the accompanying drawings, the robotic system is susceptible of several changes without departing from the scope of protection defined in the following claims.

The invention claimed is:

1. A robotic system for laparoscopic surgery comprising:
    a supporting structure comprising a vertical column having a longitudinal axis extending therethrough; and,
    a number of arms that can be rotated independently of each other around the longitudinal axis of the column, said arms being slidably attached to the column; said arms comprising:
    a first member and
    a second member;
    the first and second members being hingedly joined to each other, and,
    the first member being rotatably hinged on the supporting structure, and,
    the first member being adapted to be rotated around a longitudinal axis of the first member and
    the second member being adapted to receive a joint having at least two degrees of freedom for attaching a tool; and
    first and second upper sections rotatably mounted to each other and to the supporting structure and arranged at different heights to each other,
    wherein
    the arms are respectively associated with the first and second upper sections so that the arms can be rotated independently of each other a full turn around a longitudinal axis of the supporting structure without interfering with each other; and
    the first and second upper sections are configured for sliding in order to independently adjust the height of the arms.

2. A robotic system as claimed in claim 1, wherein said longitudinal axis of the first member is at least substantially perpendicular to a joint axis for the hinged joining of the first member and the second member to each other.

3. A robotic system as claimed in claim 1, wherein the joint having at least two degrees of freedom for attaching a tool is a gimbal-type joint.

4. A robotic system as claimed in claim 1, wherein the second member of each of the arms consists of two parts to which the first member of each of the arms is hinged.

5. A robotic system as claimed in claim 1 wherein at least two of said number of arms are hinged on said supporting structure.

6. A robotic system as claimed in claim 1, wherein the first member is rotatably mounted on an extension integral with the supporting structure.

* * * * *